United States Patent
Wada (10) Patent No.: US 10,835,712 B2
(45) Date of Patent: Nov. 17, 2020

(54) MEDICAL TUBE

(71) Applicant: TERUMO KABUSHIKI KAISHA, Shibuya (JP)

(72) Inventor: Satoshi Wada, Shizuoka (JP)

(73) Assignee: TERUMO KABUSHIKI KAISHA, Shibuya (JP)

(*) Notice: Subject to any disclaimer, the term of this patent is extended or adjusted under 35 U.S.C. 154(b) by 228 days.

(21) Appl. No.: 15/263,973

(22) Filed: Sep. 13, 2016

(65) Prior Publication Data

US 2016/0375222 A1 Dec. 29, 2016

Related U.S. Application Data (63) Continuation of application No. PCT/JP2015/054918, filed on Feb. 23, 2015.

(30) Foreign Application Priority Data

Mar. 14, 2014 (JP) ................... 2014-051405

(51) Int. Cl.
*A61M 25/00* (2006.01)
*A61M 39/22* (2006.01)
*A61M 25/06* (2006.01)

(52) U.S. Cl.
CPC .... *A61M 25/0054* (2013.01); *A61M 25/0097* (2013.01); *A61M 25/0662* (2013.01);
(Continued)

(58) Field of Classification Search
CPC .......... A61M 25/0054; A61M 25/0097; A61M 25/0051; A61M 2025/0059;
(Continued)

(56) References Cited

U.S. PATENT DOCUMENTS 5,466,230 A  11/1995 Davila
5,897,537 A * 4/1999 Berg ............... A61M 25/0009
                                      138/134

(Continued)

FOREIGN PATENT DOCUMENTS

JP  59-014601 U   1/1984
JP  8-071161 A    3/1996
(Continued)

OTHER PUBLICATIONS

International Search Report (PCT/ISA/210) issued on May 26, 2015, by the Japanese Patent Office as the International Searching Authority for International Application No. PCT/JP2015/054918.
(Continued)

*Primary Examiner* — Manuel A Mendez
*Assistant Examiner* — Justin L Zamory
(74) *Attorney, Agent, or Firm* — Buchanan Ingersoll & Rooney PC (57) ABSTRACT

A medical tube including a flexible tube-shaped main body, a hub connected to the proximal portion of the tube-shaped main body, and a strain relief member supported at a distal portion of the hub. The strain relief member surrounds a predetermined portion of the proximal portion of the tube-shaped main body. The tube-shaped main body includes a flexible portion which possesses increased flexibility for bending. The flexible portion includes at least one groove extending in a circumferential direction in the outer circumferential surface of the tube-shaped main body over a predetermined range in an axial direction of the tube-shaped main body from a position distal of the distal-most end of the strain relief member to a position proximal of the distal-most end of the strain relief member.

19 Claims, 4 Drawing Sheets

(52) U.S. Cl.
CPC ....... *A61M 39/22* (2013.01); *A61M 2025/006* (2013.01); *A61M 2025/0059* (2013.01); *A61M 2025/0098* (2013.01); *A61M 2025/0681* (2013.01)

(58) Field of Classification Search
CPC .. A61M 2025/0098; A61M 2025/0681; A61M 39/22
See application file for complete search history.

(56) References Cited

U.S. PATENT DOCUMENTS

| | | | |
|---|---|---|---|
| 7,001,369 | B2 | 2/2006 | Griffin et al. |
| 8,409,114 | B2 * | 4/2013 | Parins ................... A61M 25/00 600/585 |
| 2002/0143291 | A1 | 10/2002 | Slater |
| 2003/0004540 | A1 * | 1/2003 | Linder .................... A61F 2/013 606/200 |
| 2006/0264904 | A1 * | 11/2006 | Kerby ............... A61M 25/0014 604/523 |
| 2010/0198160 | A1 | 8/2010 | Voss |
| 2012/0071833 | A1 | 3/2012 | Hill et al. |

FOREIGN PATENT DOCUMENTS

| | | |
|---|---|---|
| JP | H08-215312 A | 8/1996 |
| JP | 2000-254235 A | 9/2000 |
| JP | 2013-22367 A | 2/2013 |

OTHER PUBLICATIONS

Written Opinion (PCT/ISA/237) dated May 26, 2015, by the Japanese Patent Office as the International Searching Authority for International Application No. PCT/JP2015/054918.

The extended European Search Report dated Sep. 21, 2017, by the European Patent Office in corresponding European Patent Application No. 15760901.7-1501. (8 pages).

* cited by examiner

MEDICAL TUBE

CROSS-REFERENCES TO RELATED APPLICATIONS

This application is a continuation of International Application No. PCT/JP2015/054918 filed on Feb. 23, 2015, and claims priority to Japanese Patent Application No. 2014-051405 filed on Mar. 14, 2014, the entire content of both of which is incorporated herein by reference.

TECHNICAL FIELD

The present invention generally relates to a medical tube having an improved kink resistance.

BACKGROUND DISCUSSION

There are various types of medical tubes (for example, catheters) that may be inserted into a living body depending on the medical purpose/need. For example, an introducer sheath used to percutaneously introduce a treatment catheter, or the like, into a living body is an example of a blood vessel indwelling catheter. In general, such a sheath includes a flexible tube-shaped main sheath body (main catheter body), a hub connected to a proximal portion of the main sheath body, and a strain relief member that surrounds a predetermined range of a proximal portion of the main sheath body to suppress the occurrence of a kink. Japanese Patent Application Publication No. 08-071161 provides an example of this type of sheath. The strain relief member is provided to another type of catheter to suppress the occurrence of a kink at a proximal portion of a main catheter body.

A medical tube such as a catheter requires compatibility between reducing a diameter to achieve a low invasion (i.e., minimal disruption/harm within the living body) and ensuring an appropriately large inner diameter to achieve a technique (i.e., a medical procedure utilizing the inner diameter). Thinning of the tube-shaped main body included in a main body of the medical tube is one way to address this need for a relatively small outer diameter and a relatively large inner diameter. However, merely thinning the tube-shaped main body increases the possibility that a kink will occur at the time of operating the medical tube.

SUMMARY

The medical tube disclosed here has been conceived in view of the above issues. The medical tube disclosed here is capable of increasing kink resistance of a tube-shaped main body while reducing a thickness of the tube-shaped main body.

The medical tube disclosed here includes a flexible tube-shaped main body, a hub connected to a proximal portion of the tube-shaped main body, and a strain relief member supported at a distal portion of the hub. The strain relief member surrounds a predetermined range of a proximal side of the tube-shaped main body. The tube-shaped main body includes a flexible portion whose flexibility for bending is increased by forming at least one groove extending in a circumferential direction in an outer circumferential portion over a predetermined range from a distal side from a most distal portion of the strain relief member to a proximal side from the most distal portion.

According to the medical tube configured as described above, flexibility for bending of the tube-shaped main body increases in the flexible portion because the flexible portion is provided in a front-rear range including the most distal portion of the strain relief member. Therefore, it is possible to increase kink resistance of the tube-shaped main body while reducing the wall thickness of the tube-shaped main body.

In the above-described medical tube, the groove extending in the circumferential direction may be a helical groove. According to this configuration, it is possible to easily form a groove extending in the circumferential direction over a predetermined range of the tube-shaped main body.

In the above-described medical tube, the flexible portion may include a plurality of sub-regions, each of which has a different pitch or width in the groove, and the sub-region on a distal side may be more flexible in the sub-regions adjacent to each other. According to this configuration, flexibility increases in stages toward the distal side, and thus it is possible to effectively suppress the occurrence of a kink.

In the above-described medical tube, at least one boundary portion between the sub-regions may be positioned on a distal side from the most distal portion of the strain relief member. According to this configuration, flexibility increases in stages toward the distal side in a front-rear region including the most distal portion of the strain relief member, and thus it is possible to more effectively suppress the occurrence of a kink.

In the above-described medical tube, the medical tube may be an introducer sheath indwelled in a lumen of a living body to introduce another elongated medical instrument into the body. In this way, it is possible to provide an introducer sheath excellent in kink resistance.

In another aspect of the medical tube disclosed here, the medical tube includes a flexible tube-shaped main body extending in an axial direction, a hub connected to the outer circumferential surface of the proximal portion of the tube-shaped main body, and a strain relief member connected to the distal portion of the hub. The strain relief member overlaps a part of the proximal portion of the tube-shaped main body in the axial direction. The strain relief member includes a tapered portion. The tapered portion has an outer diameter that gradually decreases from the proximal end to the distal end. The tube-shaped main body includes a flexible portion which has at least one circumferentially extending groove in the outer circumferential surface of the tube-shaped main body. The flexible portion axially extends over a predetermined range of the tube-shaped main body. The groove (or multiple grooves) defines a distal end and a proximal end of the predetermined range of the tube-shaped main body. The distal end of the predetermined range of the tube-shaped main body is at a first location on the tube-shaped main body that is distal to the distal-most end of the strain relief member, and the proximal end of the predetermined range is at a second location on the tube-shaped main body that is proximal to the distal-most end of the strain relief member. The tapered portion of the strain relief member axially overlaps the second location of the tube-shaped main body.

According to the medical tube disclosed here, it is possible to increase kink resistance of the tube-shaped main body while reducing a wall thickness.

DETAILED DESCRIPTION

A medical tube according to the described aspects of the present disclosure will be described in detail below, with reference to the embodiments in the attached drawings. These embodiments represent examples of the inventive medical tube disclosed here.

Figure 1:
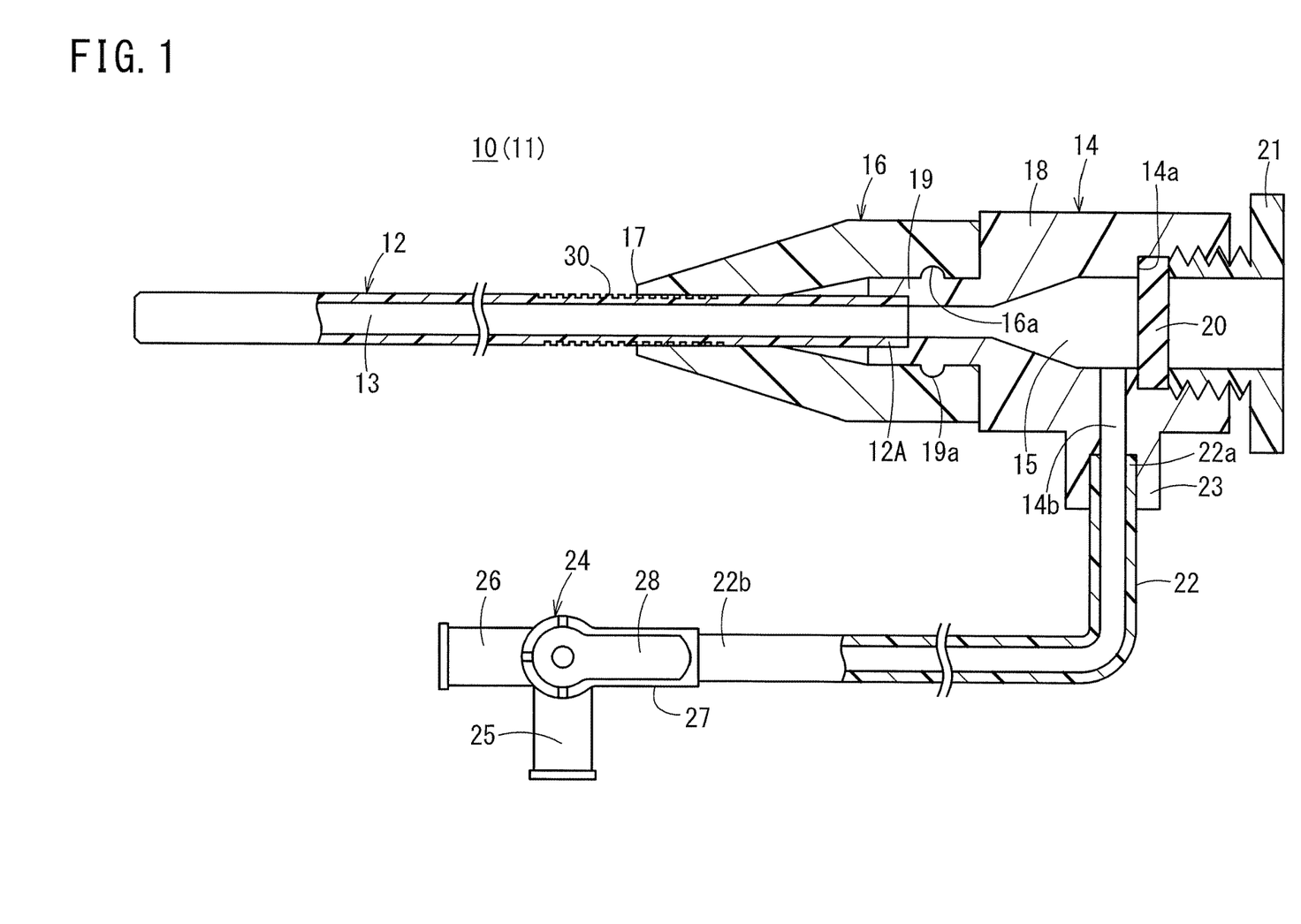
FIG. 1 is a partially-omitted schematic diagram of an embodiment of a medical tube (catheter).

FIG. 1 is a partially-omitted schematic diagram of a catheter 10 included in a medical tube according to an embodiment of the invention. The catheter 10 is a medical instrument that is inserted into a lumen in a living body such as a blood vessel. The catheter 10 is configured as an introducer sheath 11 in the embodiment illustrated in FIG. 1. The introducer sheath 11 is a device used in combination with a dilator (not illustrated) to introduce a treatment catheter or the like percutaneously into the living body. The catheter 10 may also be a different catheter than the introducer sheath 11. For example, the catheter 10 may be a treatment catheter such as a balloon catheter, a guiding catheter, or the like.

As illustrated in FIG. 1, the catheter 10 includes a main catheter body 12 (tube-shaped main body), a hub 14, and a strain relief member 16. The main catheter body 12 is a flexible tube-shaped member (i.e., an elongated member possessing flexibility) and is also referred to as a shaft. When the catheter 10 is an introducer sheath 11, the main catheter body 12 is also referred to as a sheath tube. The main catheter body 12 includes a lumen 13 that is open at a distal end and open at a proximal end of the main catheter body 12.

A length of the main catheter body 12 varies according to the type (intended use) of the catheter 10. For example, in the case of the introducer sheath 11, the length is in a range of about 20 to 800 mm.

Examples of a material used to make the main catheter body 12 include polyvinyl chloride-based resin, a urethane resin such as polyurethane, an olefin-based resin such as polyethylene, polyamide, and a synthetic resin such as ethylene-vinyl acetate copolymer, silicone rubber, and latex rubber.

The hub 14 is a member that includes a lumen 15 connected to a proximal portion 12A of the main catheter body 12 to communicate with the lumen 13 of the main catheter body 12. The hub 14 includes a protruding portion 19 which possesses a reduced outer diameter relative to a body portion 18 of the hub 14. The protruding portion 19 is protrudes in a distal end direction at a distal end of the hub 14 (i.e., protrudes distally at the distal end of the hub 14). The proximal portion 12A of the main catheter body 12 is inserted into and fixed to an inner peripheral portion at the distal end of the protruding portion 19. Examples of a material used to make the hub 14 include a rigid resin such as polypropylene, ABS, and polycarbonate.

The hub 14 includes a valve body 20 inside of the hub 14. The valve body 20 is for preventing liquid from leaking from the inside of the hub 14. A hollow fixing member 21 is screwed into a proximal portion of the hub 14, and the valve body 20 is fixed inside the hub 14 when the valve body 20 is interposed between a distal end surface of the fixing member 21 and a step portion 14a formed inside the hub 14 (i.e., a proximal surface of the valve body 20 contacts and is held in place by the distal end surface of the fixing member 21 and a distal surface of the valve body 20 contacts and is held is place against the step portion 14a of the hub 14). The fixing of the fixing member 21 to the proximal portion of the hub 14 is not restricted to screwing. Another structure capable of interposing (holding) the valve body 20 between the hub 14 and the fixing member 21 may be used. For example, the fixing member 21 may be bonded or heat-welded to the hub 14 such that the valve body 20 is interposed between the hub 14 and the fixing member 21. In addition, the valve body 20 may be provided in a connector member connectable to a proximal end of the hub 14 instead of providing the valve body 20 directly in the hub 14.

The valve body 20 possesses an elastic material (for example, silicone rubber). A slit (not illustrated), into which a dilator or another catheter can be inserted, is formed in the valve body 20. The valve body 20 may prevent a body fluid (blood or the like) flowing in the lumen 15 of the hub 14 through the main catheter body 12 from leaking out when the dilator (or the like) is inserted into the slit.

A flexible side tube 22 is connected to a side portion of the hub 14. In the embodiment illustrated in FIG. 1, one end of the side tube 22 is connected to a side port 23 extruding outward from the side portion of the hub 14 (i.e., the side port 23 extends radially outward from an outer circumferential surface of the hub 14). A lumen of the side tube 22 communicates with the lumen 15 of the hub 14 through a side hole 14b provided in the hub 14.

A three-way stopcock 24 is provided at an end portion 22b of the side tube 22 on the opposite side from an end portion 22a connected to the hub 14 (i.e., connected to the side port 23 of the hub 14). The three-way stopcock 24 may include, for example, a port 25 for discharging air, a port 26 for chemical injection to which a syringe, or the like (not illustrated) is connected, a port 27 connected to the end portion 22b of the side tube 22, and a cock 28 for switching communication states of the ports 25, 26, and 27. The port 25 and the port 26 are not restricted to uses for discharging air and chemical injection and may be used for other purposes.

The strain relief member 16 has a function of preventing or suppressing a kink (bending) at a proximal side or proximal portion of the main catheter body 12 (specifically, an interlock portion of the main catheter body 12 and the hub 14 and a region around the interlock portion). As illustrated in FIG. 1, the strain relief member 16 is a hollow member having flexibility which is supported at a distal portion of the hub 14 (protruding portion 19) and surrounds a predetermined range of the proximal side of the main catheter body 12.

The strain relief member 16 possesses a relatively large outer diameter at a proximal end portion and a relatively small outer diameter at a distal end portion. The outer diameter of the strain relief member 16 gradually decreases toward the distal end (i.e., at least a portion of the strain relief member 16 is tapered). A wall thickness of the strain relief member 16 decreases toward the distal side. A proximal portion of the strain relief member 16 is fit onto the protruding portion 19 provided at the distal end of the hub 14. In this way, the strain relief member 16 is supported by the distal portion of the hub 14.

A bulge portion 19a annularly extending in a circumferential direction (i.e., extending radially outward) is formed on an outer peripheral surface of the protruding portion 19 in FIG. 1. The strain relief member 16 is thus prevented from falling off of (i.e., separating from) the protruding portion 19 when the bulge portion 19a is engaged with an annular depression 16a formed on an inner peripheral surface of the proximal portion of the strain relief member 16.

Examples of a material used to make the strain relief member 16 include a thermoplastic resin such as styrene resin, olefin resin, and polyester resin.

Figure 2:
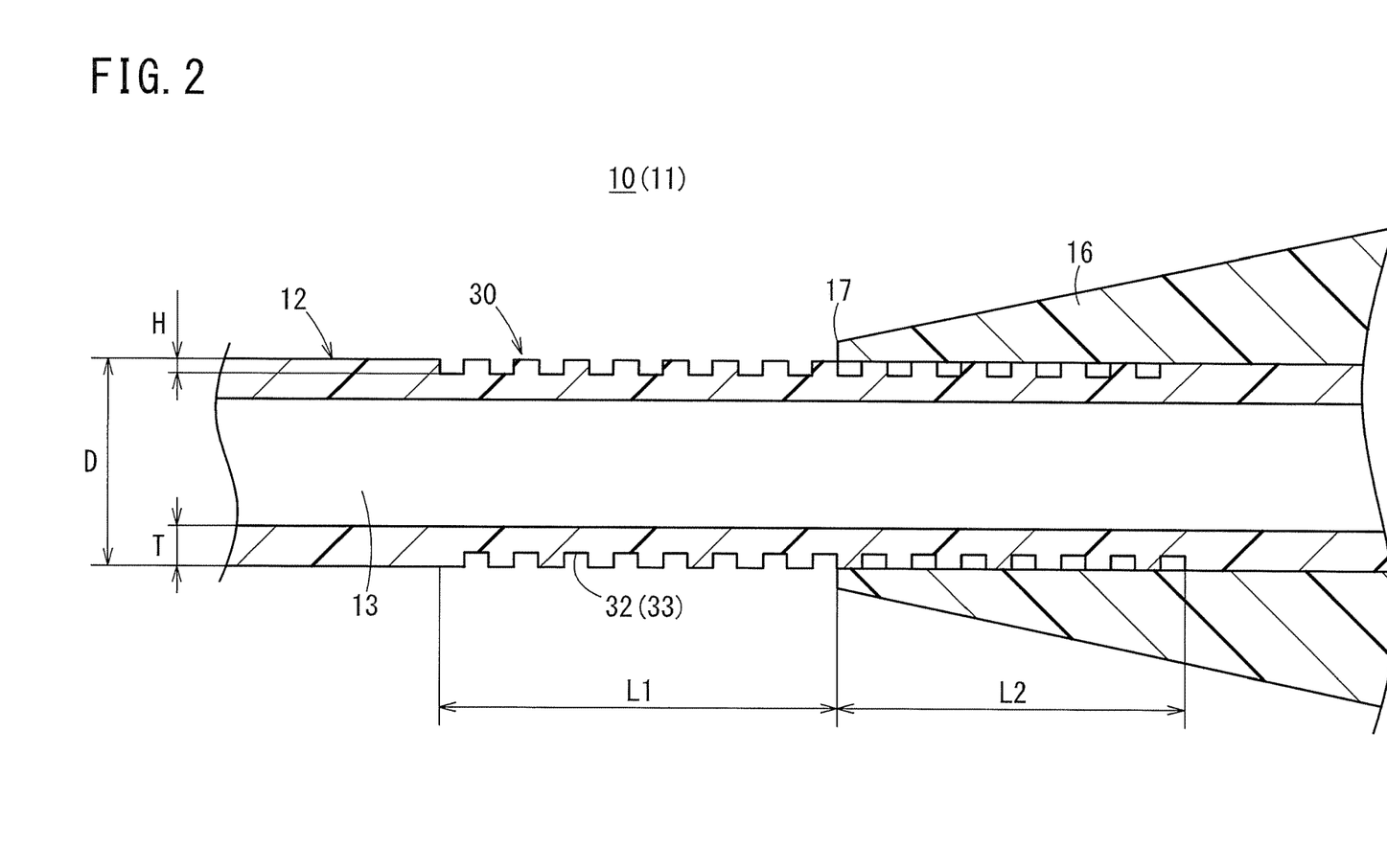
FIG. 2 is a longitudinal sectional view including a main catheter body of the catheter illustrated in FIG. 1.

As illustrated in FIG. 2, the main catheter body 12 includes a flexible portion 30 (i.e., a less rigid or softer portion) whose flexibility for bending is increased compared to front and rear parts of the catheter main body 12 (i.e., compared to portions of the catheter main body 12 that are distal and proximal of the flexible portion 30) by forming at least one groove 32 (i.e., a recess or trench) extending in the circumferential direction in an outer circumferential portion over a predetermined range. The predetermined range of the main catheter body 12 extends from a portion of the main catheter body 12 that is distal to a most distal portion 17 (i.e., a distal-most portion) of the strain relief member 16 to another portion of the main catheter body 12 that is proximal to the most distal portion 17 (i.e., proximal to the distal-most portion 17).

The groove 32 is a portion indented by a depth H with respect to an outer diameter D (reference outer diameter) of the main catheter body 12. Therefore, a wall thickness of a portion of the main catheter body 12 in which the groove 32 is formed is thinner than a wall thickness T of a portion other than the flexible portion 30 by the depth H of the groove 32. The flexible portion 30 has higher flexibility than that of the front and rear parts of the softness portion 30 in the main catheter body 12 because of the groove 32.

In the embodiment illustrated in FIG. 2, the groove 32 extending in the circumferential direction is a helical groove 33. The helical groove 33 may be a single helix or a multiple helix such as a double helix. The helical groove 33 may be a groove which is not continuous from a distal end to a proximal end of the flexible portion 30 and may be intermittent (interrupted) at one or more places in the middle. The groove 32 may be an annular groove instead of the helical groove 33, and a plurality of (multiple) annular grooves may be formed in the outer circumferential portion of the main catheter body 12 at intervals along an axial direction.

The depth H of the groove 32 may be 5 to 50% with respect to the thickness T of the wall that forms the main catheter body 12. The depth H of the groove 32 more preferably may be 20 to 40% relative to the thickness of the wall T. Alternatively, even though the depth H of the groove 32 depends on the thickness T of the wall that forms the main catheter body 12, for example, the depth H may be set to about 30 to 100 µm.

The distance L1 from the most distal portion 17 of the strain relief member 16 to a most distal portion (i.e., distal-most portion) of the flexible portion 30 (i.e., the distal-most portion of the groove 32) may be 5 to 50 mm, preferably 10 to 30 mm. The distance L2 from the most distal portion 17 of the strain relief member 16 to the most proximal portion of the flexible portion 30 (i.e., the proximal-most portion of the groove 32) may be 5 to 50 mm, preferably 10 to 30 mm.

The helical groove 33 may be formed by helicoidally winding a linear member (wire or the like) around an outer peripheral surface of a tube-shaped compact (which is supported by a spindle and has the outer diameter D (the main catheter body 12 before the flexible portion 30 is formed)) along a predetermined range in an axial direction, heating the linear member, and then removing the linear member. Note that the groove 32 may be formed by helicoidally or annularly scraping the outer peripheral surface of the compact instead of using the above-described method using the linear member. Alternatively, the main catheter body 12 including the groove 32 may be manufactured by injection molding using an injection molding tool that possesses a shape corresponding to the groove 32 in advance.

Operations and effects of the catheter 10 will be described below.

As described above, the catheter 10 is configured as an introducer sheath 11. In the use of the introducer sheath 11, the introducer sheath 11 is combined with a dilator (not illustrated). Specifically, an assembly (introducer) in which the dilator is positioned in the introducer sheath 11 punctures a blood vessel of a patient such that a distal end of the introducer sheath 11 secures or punctures the blood vessel. Thereafter, the main catheter body 12 is further inserted into the blood vessel and inserted up to a portion around the most distal portion 17 of the strain relief member 16. The dilator is then pulled out of the introducer sheath 11. A length of the main catheter body 12 inserted into or positioned in the blood vessel is set to a predetermined length.

Subsequently, another device such as a treatment catheter (balloon catheter or the like) or a guiding catheter is introduced through or into the introducer sheath 11 while being led by a guide wire (not illustrated) inside the blood vessel. The device is advanced up to a predetermined region inside the living body, and treatment is performed.

The proximal-side portion of the main catheter body 12 (the interlock portion of the main catheter body 12 and the hub 14) is exposed to the outside of the body during a surgery. Thus, when the main catheter body 12 is inserted into the blood vessel, or when the hub 14 may be lifted to insert and remove another device from a proximal end opening of the hub 14, bending stress acts on the proximal-side portion of the main catheter body 12. The strain relief member 16 is thus provided to suppress the occurrence of a kink (i.e., kinking) in the proximal-side portion of the main catheter body 12 due to bending stress at this time.

However, a kink may occur when the amount of change of the main catheter body 12 bending is greater than or equal to a certain amount. In particular, around a distal portion of the strain relief member 16, (that is, around a boundary portion between a portion covered with the strain relief member 16 and a portion not covered with the strain relief member 16 in the main catheter body 12) bending rigidity greatly varies, and stress is easily concentrated. Thus, a kink more easily occurs in this location.

The catheter 10 thus includes the flexible portion 30, the flexibility of which is increased by the groove 32, in a front-rear range including the most distal portion 17 of the strain relief member 16 in the main catheter body 12 (i.e., the distal-most end of the flexible portion 30 is distal to the distal most portion 17 of the strain relief 16 and the proximal-most end of the flexible portion 30 is proximal to the distal-most portion 17 of the strain relief 16). The flexible portion 30 has higher flexibility than that of the portion of the main catheter body 12 in which the groove 32 is not provided. Specifically, the flexible portion 30 is more flexible than a portion of the catheter main body 12 distal to the flexible portion and a portion of the catheter main body 12 proximal to the flexible portion 30.

Since the flexible portion 30 is provided in the main catheter body 12, the main catheter body 12 having the flexible portion 30 is more flexible with respect to bending when compared at the same outer diameter D (i.e., a portion of the main catheter body 12 other than the flexible portion 30 that has outer diameter D is less flexible or more rigid than the flexible portion 30 having the same outer diameter D). When compared at the same outer diameter D, the amount of change of bending at which a kink may occur (allowed amount of change) is larger in the main catheter body 12 having the flexible portion 30 than in a conventional main catheter body not having the flexible portion 30.

As described above, a more flexible portion of the catheter 10 (that is, a less rigid portion than another portion in the axial direction) is provided in a particular region of the proximal portion of the main catheter body 12 and is allowed to be easily bent. The more flexible portion of the catheter 10 thereby suppresses stress concentration due to bending and inhibits the occurrence of a kink. Therefore, according to the catheter 10, kink resistance of the main catheter body 12 may be increased while reducing the wall thickness of the main catheter body 12.

The groove 32, which is provided in the outer circumferential portion of the main catheter body 12 and extends in the circumferential direction, is may be a helical groove 33 as illustrated in FIG. 2. As described above, for example, since the helical groove 33 is easily formed by winding a linear member around the outer circumferential portion of the tube-shaped compact, it is possible to easily manufacture the main catheter body 12 having the flexible portion 30 over the predetermined range in the axial direction.

When the introducer sheath 11 is indwelled inside the blood vessel, the main catheter body 12 is inserted into the blood vessel up to a portion around the most distal portion 17 of the strain relief member 16. A portion around the strain relief member 16 of the main catheter body 12 may thus come into contact with a skin or a blood vessel wall. The degree of curvature locally increases relatively easily in the portion. Thus, a kink may easily occur in this portion. For this reason, the medical tube disclosed here is capable of suppressing a kink in the proximal-side portion of the main catheter body 12 and is thus suitable when used for the introducer sheath 11.

Figure 3:
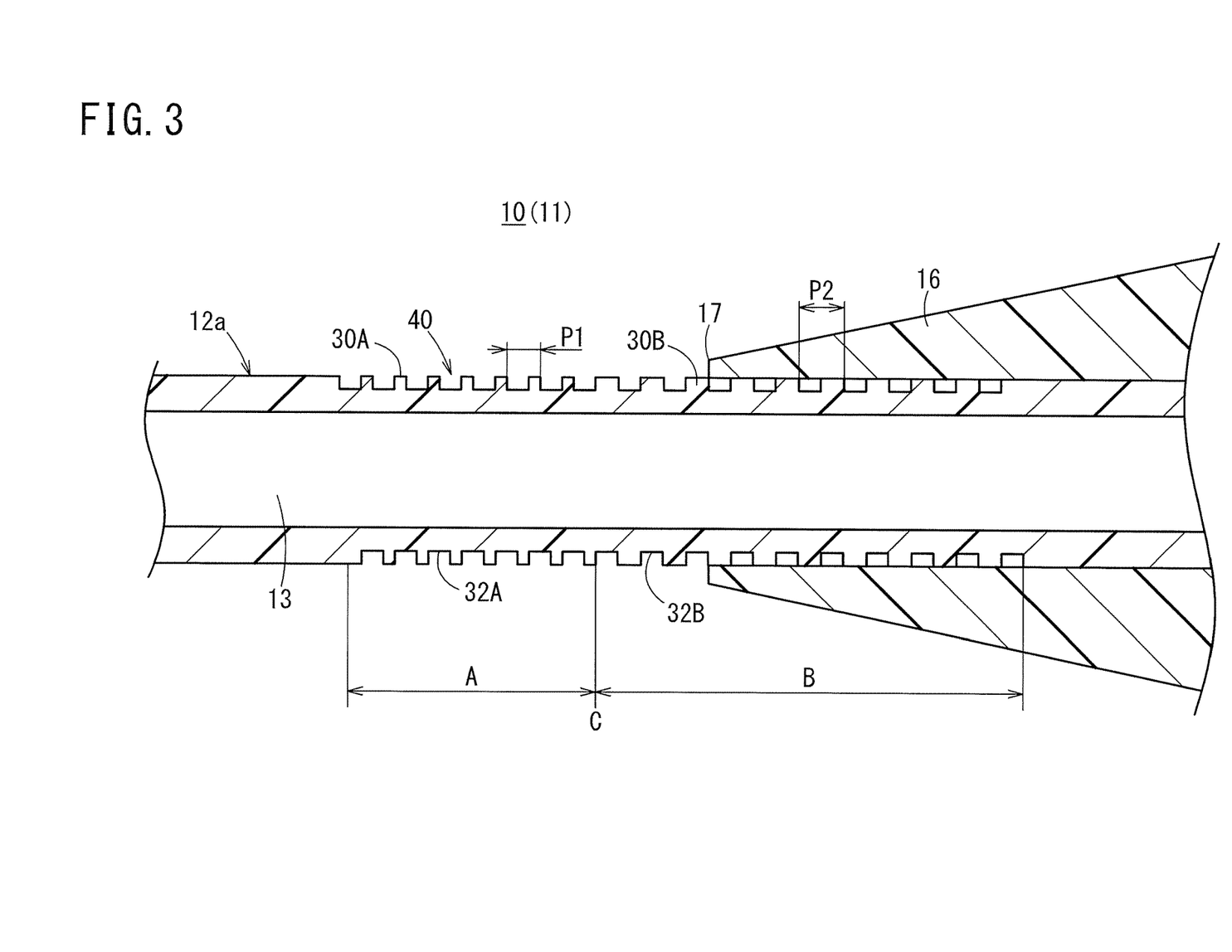
FIG. 3 is a longitudinal sectional view including a main catheter body according to a first modified example.

A plurality of sub-regions 30A and 30B having different groove pitches may be provided in a flexible portion 40 of a main catheter body 12a according to a first modified example illustrated in FIG. 3. The sub-region 30A on a distal side in the embodiment illustrated in FIG. 3 is more flexible than where the sub-regions 30A and 30B are adjacent to each other (and thus the sub-region 30A is also more flexible than the sub-region 30B on the proximal side). At least one boundary portion C between the sub-regions 30A and 30B (i.e., the area transitioning between one sub-region 30A and another sub-region 30B) is positioned on the distal side from a most distal portion 17 of a strain relief member 16 (i.e., distal to the distal-most end of the strain relief member 16).

As illustrated in FIG. 3, the flexible portion 30 includes the first sub-region 30A, in which a groove 32A is formed at a relatively small pitch P1, and the second sub-region 30B, in which a groove 32B is formed at a relatively large pitch P2. Therefore, the first sub-region 30A has higher flexibility with respect to bending than the flexibility of the second sub-region 30B. The range indicated by A in FIG. 3 refers to the first sub-region 30A and a range indicated by B refers to the second sub-region 30B in FIG. 3.

Meanwhile, flexibility obtained by applying rigidity of the strain relief member 16 to the main catheter body 12a is higher in a portion from a boundary portion C between the first sub-region 30A and the second sub-region 30B to the most distal portion 17 of the strain relief member 16 than in a portion from the most distal portion 17 of the strain relief member 16 to a most proximal portion of the second sub-region 30B.

Each of the grooves 32A and 32B in the first sub-region 30A and the second sub-region 30B of the embodiment illustrated in FIG. 3 is a helical groove. Each of the grooves 32A and 32B may correspond to a plurality of annular grooves formed at intervals in an axial direction in place of the helical groove. The groove 32A of the first sub-region 30A and the groove 32B of the second sub-region 30B may communicate with each other or may be independent from each other (i.e., do not communicate with one another).

Flexibility of the embodiment illustrated in FIG. 3 increases in stages toward the distal side in a front-rear region including the most distal portion 17 of the strain relief member 16 because the flexible portion 40 includes a plurality of sub-regions 30A and 30B having different groove pitches. The configuration of the embodiment illustrated in FIG. 3 makes it possible to more effectively suppress the occurrence of a kink in the main catheter body 12a. In alternative embodiments, three or more sub-regions having different groove pitches may be provided in the main catheter body 12a.

Figure 4:
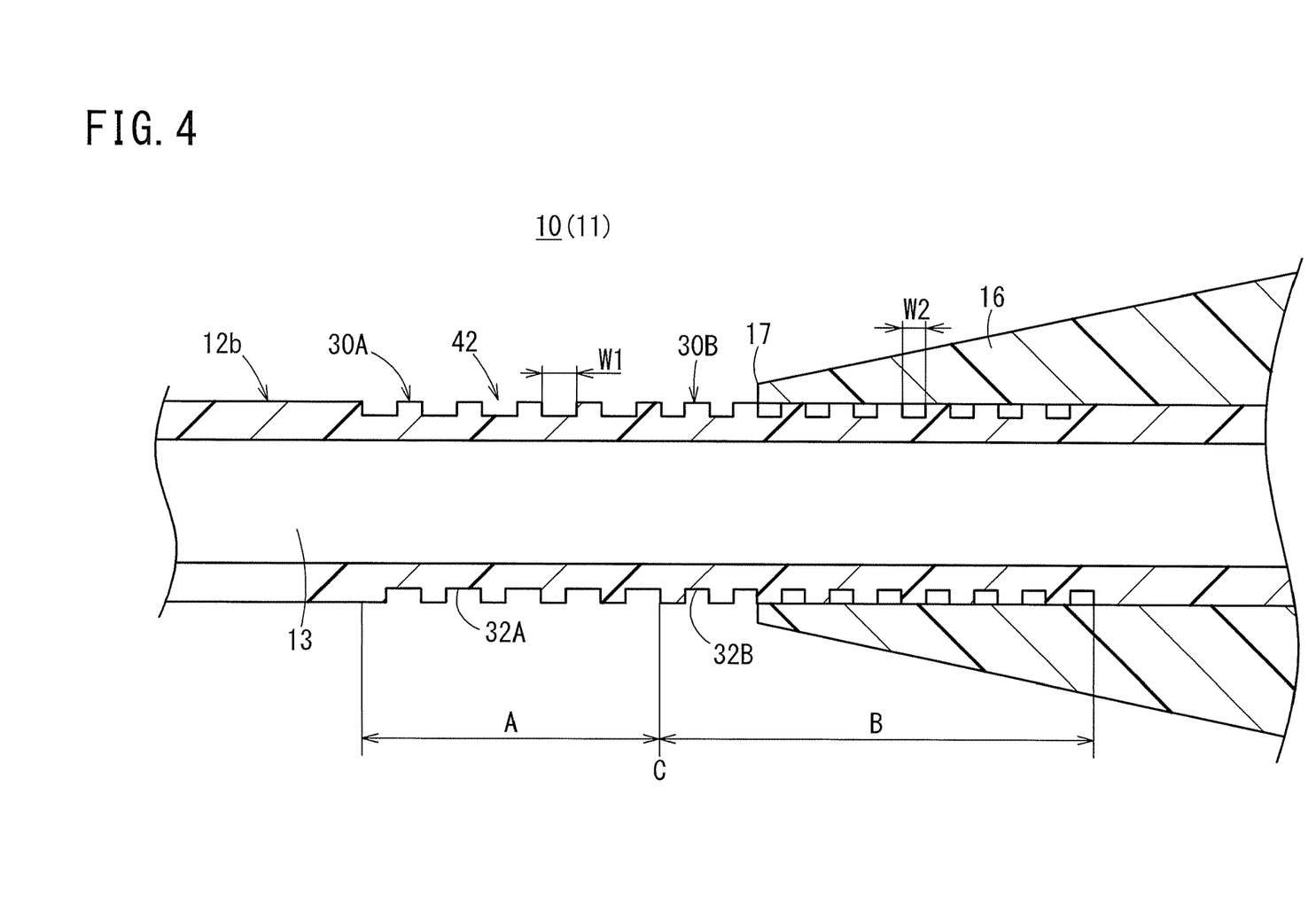
FIG. 4 is a longitudinal sectional view including a main catheter body according to a second modified example.

FIG. 4 illustrates a second modified example of an embodiment of the medical tube disclosed here. The flexible portion 42 of a main catheter body 12b according to the embodiment illustrated in FIG. 4 includes a first sub-region 30A that may have higher flexibility with respect to bending than that of a second sub-region 30B. The higher flexibility of the first sub-region 30A may be obtained by setting a width W1 of a groove 32A of the first sub-region 30A to be larger than a width W2 of a groove 32B of the second sub-region 30B. The same effect as that of a configuration of FIG. 3 is obtained by a configuration of FIG. 4. In alternative embodiments, three or more sub-regions having different groove widths may be provided in the main catheter body 12b.

Even though the medical tube has been described above using the preferred embodiment, the invention is not restricted to the embodiment, and may be variously modified within a range not departing from a subject matter of the invention.

The detailed description above describes a medical tube. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical tube comprising:
    a flexible tube-shaped main body possessing a distal portion, a proximal portion, an inner circumferential surface and an outer circumferential surface, the flexible tube-shaped main body comprising a lumen extending throughout a longitudinal extent of the tube-shaped main body;
    a hub connected to the proximal portion of the tube-shaped main body;
    a strain relief member supported at a distal portion of the hub, the strain relief member surrounding a predetermined portion of the proximal portion of the tube-shaped main body, the strain relief member possessing a distal-most end;
    the tube-shaped main body comprising a flexible portion which possesses increased flexibility for bending, the flexible portion including at least one groove extending in a circumferential direction in the outer circumferential surface of the tube-shaped main body over a predetermined range in an axial direction of the tube-shaped main body from a position distal of the distal-most end of the strain relief member to a position proximal of the distal-most end of the strain relief member; and the flexible tube-shaped main body being formed in one piece as a unitary structure with the inner circumferential surface directly exposed to the lumen, the flexible tube-shaped main body being monolithic.

2. The medical tube according to claim 1, wherein the groove extending in the circumferential direction is helical groove.

3. The medical tube according to claim 1, wherein the flexible portion includes a plurality of sub-regions, each of the sub-regions having a groove width that is different than the groove width of the other sub-regions.

4. The medical tube according to claim 3, wherein one of the sub-regions on a distal side is more flexible than another sub-region on a proximal side.

5. The medical tube according to claim 3, wherein at least one boundary portion between adjacent sub-regions is positioned distal to the distal-most end of the strain relief member.

6. The medical tube according to claim 1, wherein the medical tube is an introducer sheath configured to indwell in a lumen of a living body to introduce an elongated medical instrument into the body.

7. A medical tube comprising:
a flexible tube-shaped main body extending in an axial direction, the tube-shaped main body possessing a distal portion, a proximal portion, an outer circumferential surface, and a proximal-most end;
a hub connected to the outer circumferential surface of the proximal portion of the tube-shaped main body, the hub possessing a distal portion and a proximal portion;
a strain relief member connected to the distal portion of the hub, the strain relief member overlapping a part of the proximal portion of the tube-shaped main body in the axial direction, the strain relief member possessing a distal-most end;
the strain relief member comprising a tapered portion which possesses a proximal end and a distal end, the tapered portion possessing an outer diameter that gradually decreases from the proximal end to the distal end;
the tube-shaped main body comprising a flexible portion, the flexible portion including a circumferentially extending helical groove in the outer circumferential surface of the tube-shaped main body, the flexible portion axially extending over a predetermined range of the tube-shaped main body, the predetermined range possessing a distal-most end and a proximal-most end, the groove extending continuously from the distal-most end of the predetermined range to the proximal-most end of the predetermined range;
the distal-most end of the predetermined range of the tube-shaped main body being at a first location on the tube-shaped main body that is distal to the distal-most end of the strain relief member and the proximal-most end of the predetermined range being at a second location on the tube-shaped main body that is proximal to the distal-most end of the strain relief member, the tapered portion of the strain relief member axially overlapping the second location of the tube-shaped main body; and
the flexible tube-shaped main body being formed in one piece as a unitary structure with the inner circumferential surface directly exposed to the lumen, the flexible tube-shaped main body being monolithic.

8. The medical tube according to claim 7, wherein the continuous helical groove possesses equally spaced helical windings throughout the predetermined range of the tube-shaped main body.

9. The medical tube according to claim 7, wherein the predetermined range possesses a length in the axial direction of at least 10 mm and no greater than 100 mm.

10. The medical tube according to claim 9, wherein a distance in the axial direction from the first location of the tube-shaped main body to the distal-most end of the strain relief member is at least 5 mm and no greater than 50 mm.

11. The medical tube according to claim 7, wherein
the tube-shaped main body possesses a wall thickness and the groove possesses a depth; and
the depth of the groove is between 5% and 50% of the wall thickness of the tube-shaped main body.

12. The medical tube according to claim 7, wherein
the hub possesses a maximum outer diameter and the strain relief member possesses a maximum outer diameter; and
the maximum diameter of the hub is greater than the maximum outer diameter of the strain relief member.

13. The medical tube according to claim 12, wherein the distal portion of the hub comprises a step portion, a proximal surface of the strain relief member contacting the step portion of the hub.

14. The medical tube according to claim 7, wherein
the tube-shaped main body comprises a first portion distal to the flexible portion and a second portion proximal to the flexible portion; and
the first and second portions of the tube-shaped main body are more rigid than the flexible portion of the tube-shaped main body.

15. A medical tube comprising:
a flexible tube-shaped main body possessing a distal portion, a proximal portion, a distal end, an inner circumferential surface and an outer circumferential surface, the flexible tube-shaped main body comprising a lumen, the distal end of the flexible tube-shaped main body being a distal end of the medical tube;
a hub connected to the proximal portion of the tube-shaped main body;
a strain relief member supported at a distal portion of the hub, the strain relief member surrounding a predetermined portion of the proximal portion of the tube-shaped main body, the strain relief member possessing a distal-most end;
the flexible tube-shaped main body comprising a flexible portion which possesses increased flexibility for bending, the flexible portion possessing a distal end and a proximal end, the flexible portion comprising a groove extending in a circumferential direction in the outer circumferential surface of the tube-shaped main body continuously over a predetermined range in an axial direction of the tube-shaped main body from the distal end of the flexible portion which is distal of the distal-most end of the strain relief member to the proximal end of the flexible portion which is proximal of the distal-most end of the strain relief member;
the flexible tube-shaped body comprising a constant outer diameter portion extending continuously in the axial direction from the distal end of the flexible portion to the distal end of the medical tube, the constant outer diameter portion possessing a constant outer diameter; and the flexible tube-shaped main body being formed at one time as a unitary structure with the inner circumferential surface directly exposed to the lumen.

16. The medical tube according to claim 1, wherein the tube-shaped main body comprises a rigid distal portion distal to the flexible portion of the tube-shaped main body, the rigid distal portion of the tube-shaped main body being more rigid than the flexible portion of the tube-shaped main body.

17. The medical tube according to claim 16, wherein the rigid distal portion extends continuously from in the axial direction from a distal end of the flexible portion to a distal end of the medical tube.

18. The medical tube according to claim 17, wherein
the rigid distal portion possesses an outer diameter, and
the outer diameter of the rigid distal portion is constant along an entirety of the rigid distal portion.

19. The medical tube according to claim 1, wherein the flexible portion of the tube-shaped main body possesses a length of 10 mm to 100 mm.

* * * * *